(12) United States Patent
Leskowicz

(10) Patent No.: US 7,407,922 B2
(45) Date of Patent: Aug. 5, 2008

US007407922B2

(54) DEODORIZING COMPOSITIONS

(75) Inventor: James J. Leskowicz, Racine, WI (US)

(73) Assignee: S.C. Johnson & Son, Inc., Racine, WI (US)

(*) Notice: Subject to any disclaimer, the term of this patent is extended or adjusted under 35 U.S.C. 154(b) by 0 days.

(21) Appl. No.: 11/250,144

(22) Filed: Oct. 13, 2005

(65) Prior Publication Data
US 2007/0083998 A1      Apr. 19, 2007

(51) Int. Cl.
*C11D 3/00*      (2006.01)

(52) U.S. Cl. .......................... 510/278; 8/137; 8/115.51; 422/5; 252/8.81; 510/276; 510/108; 510/109

(58) Field of Classification Search .............. 8/115.51, 8/137; 510/507, 509, 349, 108, 109, 276, 510/278; 252/135, 8.81; 422/5
See application file for complete search history.

(56) References Cited

U.S. PATENT DOCUMENTS

| | | | |
|---|---|---|---|
| 2,582,395 A | 1/1952 | Rigby | |
| 2,742,396 A | 4/1956 | Sperandio et al. | |
| 2,765,305 A | 10/1956 | Cronheim et al. | |
| 2,882,243 A | 4/1959 | Milton | |
| 3,466,257 A | 9/1969 | Coulson | |
| 3,943,132 A | 3/1976 | Schirmann et al. | |
| 4,027,346 A | 6/1977 | Wada et al. | |
| 4,064,062 A | 12/1977 | Yurko | |
| 4,304,675 A * | 12/1981 | Corey et al. ................... | 8/142 |
| 4,437,429 A | 3/1984 | Goldstein et al. | |
| 4,452,820 A | 6/1984 | D'Amelia et al. | |
| 4,493,781 A | 1/1985 | Chapman et al. | |
| 4,592,855 A | 6/1986 | Gioffre et al. | |
| 4,604,110 A | 8/1986 | Frazier | |
| 4,639,367 A | 1/1987 | Mackles | |
| 4,648,882 A | 3/1987 | Osberghaus et al. | |
| 4,648,977 A | 3/1987 | Garg et al. | |
| 4,659,494 A | 4/1987 | Soldanski et al. | |
| 4,663,068 A | 5/1987 | Hagemann et al. | |
| 4,666,940 A | 5/1987 | Bischoff et al. | |
| 4,752,465 A | 6/1988 | Mackles | |
| 4,793,833 A | 12/1988 | Lok et al. | |
| 4,795,482 A | 1/1989 | Gioffre et al. | |
| 4,826,497 A | 5/1989 | Marcus et al. | |
| 4,834,900 A | 5/1989 | Soldanski et al. | |
| 4,889,709 A | 12/1989 | Mackles et al. | |
| 5,009,668 A | 4/1991 | Berendt et al. | |
| 5,286,400 A | 2/1994 | Paszek et al. | |
| 5,296,214 A | 3/1994 | Gaffar | |
| 5,322,683 A | 6/1994 | Mackles et al. | |
| 5,358,955 A | 10/1994 | Brooks et al. | |
| 5,386,011 A | 1/1995 | Wiedeman et al. | |
| 5,387,671 A | 2/1995 | Kawai et al. | |
| 5,424,080 A | 6/1995 | Synosky et al. | |
| H1468 H | 8/1995 | Costa et al. | |
| 5,610,130 A | 3/1997 | Thomas et al. | |
| 5,610,189 A | 3/1997 | Whiteley | |
| 5,679,677 A | 10/1997 | Pill et al. | |
| 5,691,296 A | 11/1997 | Agar et al. | |
| 5,691,303 A | 11/1997 | Pan et al. | |
| 5,756,555 A | 5/1998 | Wesch et al. | |
| 5,783,543 A | 7/1998 | Fleckenstein et al. | |
| 5,844,003 A | 12/1998 | Tatton et al. | |
| 5,854,194 A | 12/1998 | Davister et al. | |
| 5,889,088 A | 3/1999 | Kisuno et al. | |
| 5,905,066 A | 5/1999 | Zocchi et al. | |
| 5,942,482 A | 8/1999 | Zocchi et al. | |
| 5,955,407 A | 9/1999 | Davister et al. | |
| 5,985,814 A | 11/1999 | Zocchi et al. | |
| 6,020,301 A | 2/2000 | Davister et al. | |
| 6,048,830 A * | 4/2000 | Gallon et al. ................ | 510/349 |
| 6,068,665 A | 5/2000 | Calton et al. | |
| 6,107,341 A | 8/2000 | Hansen et al. | |
| 6,150,321 A | 11/2000 | Davister et al. | |
| 6,172,032 B1 | 1/2001 | Davister et al. | |

(Continued)

FOREIGN PATENT DOCUMENTS

DE      4411047      10/1995

(Continued)

OTHER PUBLICATIONS

Baker et al., "The pyrolysis of non-volatile tobacco ingredients using a system that simulates cigarette combustion conditions", *Journal of Analytical an Applied Pyrolysis*, vol. 74, Iss. 1-2, Aug. 2005, printed from www.sciencedirect.com.
Linduska et al. "Tests of materials for the control of chiggers on the ground", Accession No. 1948:28251, *Journal of Economic Entomology*, 41 (1948).
Baker et al., "The effect of tobacco ingredients on smoke chemistry. Part I: Flavourings and additives", *Food and Chemical Toxicology*, vol. 42, Suppl. 1; Abstract 2 pages (2004), printed from www.sciencedirect.com.
International Search Report in PCT/US2006/040185 dated Feb. 9, 2007.
Written Opinion in PCT/US2006/040185 dated Feb. 9, 2007.

*Primary Examiner*—Lorna M. Douyon
*Assistant Examiner*—Tri V Nguyen

(57) ABSTRACT

In one aspect of the present invention a deodorizing composition comprising an effective amount of an inorganic salt, at least one odor-counteracting material, and an optional additive is provided. In another aspect of the present invention a method of using an inorganic salt, at least one of a malodor counteractant, an odor absorbent, and an odor-masking agent, and an optional additive in a solid composition for removing a malodor from a textile is provided. In yet another aspect of the present invention, a process for removing a malodor from a textile is provided. The present invention comprises compositions and kits based thereon, and methods for the preparation and use thereof.

18 Claims, No Drawings

U.S. PATENT DOCUMENTS

| | | |
|---|---|---|
| 6,284,232 B1 | 9/2001 | Calton et al. |
| 6,303,555 B1 | 10/2001 | Davister et al. |
| 6,376,542 B1 | 4/2002 | Hansen et al. |
| 6,576,601 B1 | 6/2003 | Mikic et al. |
| 6,608,024 B1 | 8/2003 | DuVal et al. |
| 6,632,830 B1 | 10/2003 | Acton et al. |
| 6,642,285 B1 | 11/2003 | Bohner |
| 6,667,299 B1 | 12/2003 | Ahlem et al. |
| 6,689,762 B1 | 2/2004 | Avramis et al. |
| 6,846,946 B2 | 1/2005 | Joyce et al. |
| 6,881,712 B2 | 4/2005 | Angell et al. |
| 6,916,781 B2 | 7/2005 | DuVal et al. |
| 6,966,696 B1 | 11/2005 | Curry et al. |
| 6,995,122 B2 | 2/2006 | Popplewell et al. |
| 7,037,887 B2 | 5/2006 | Frankenbach et al. |
| 7,056,877 B2 | 6/2006 | Caswell et al. |
| 2002/0040503 A1 | 4/2002 | Pace et al. |
| 2002/0068721 A1 | 6/2002 | Weigele et al. |
| 2003/0024997 A1 | 2/2003 | Welch et al. |
| 2003/0104969 A1 | 6/2003 | Caswell et al. |
| 2003/0139310 A1 | 7/2003 | Smith et al. |
| 2003/0158435 A1 | 8/2003 | Joyce et al. |
| 2003/0190355 A1 | 10/2003 | Hermelin et al. |
| 2003/0215513 A1 | 11/2003 | Fyhr et al. |
| 2004/0001871 A1 | 1/2004 | Boothman et al. |
| 2004/0116325 A1 | 6/2004 | Goodacre et al. |
| 2004/0126295 A1 | 7/2004 | Joyce et al. |
| 2004/0136770 A1 | 7/2004 | Muhr-Sweeney |
| 2004/0138175 A1 | 7/2004 | Madge et al. |
| 2004/0175535 A1 | 9/2004 | Bell |
| 2004/0223995 A1 | 11/2004 | Emslie et al. |
| 2004/0235705 A1 | 11/2004 | Popplewell et al. |
| 2004/0235798 A1 | 11/2004 | Murthi et al. |
| 2004/0236131 A1 | 11/2004 | Joyce et al. |
| 2005/0026793 A1 | 2/2005 | Caswell et al. |
| 2005/0037937 A1 | 2/2005 | Pace et al. |
| 2005/0070457 A1 | 3/2005 | DuVal et al. |
| 2005/0075267 A1 | 4/2005 | DuVal et al. |
| 2005/0089540 A1 | 4/2005 | Uchiyama et al. |
| 2005/0096251 A1 | 5/2005 | Frankenbach et al. |
| 2005/0106214 A1 | 5/2005 | Chen |
| 2005/0113267 A1 | 5/2005 | Popplewell et al. |
| 2005/0145711 A1 | 7/2005 | Blondeau et al. |
| 2005/0147455 A1 | 7/2005 | Muhr-Sweeney |
| 2005/0176611 A1 | 8/2005 | Caswell et al. |
| 2005/0202990 A1 | 9/2005 | Caswell et al. |
| 2005/0232881 A1 | 10/2005 | Franklin et al. |
| 2005/0281879 A1 | 12/2005 | Chen et al. |
| 2006/0018567 A1 | 1/2006 | Curry et al. |

FOREIGN PATENT DOCUMENTS

| | | |
|---|---|---|
| EP | 0 031 455 | 7/1981 |
| EP | 0031455 A1 | 7/1981 |
| EP | 0 061 876 | 10/1982 |
| EP | 0061876 A | 10/1982 |
| EP | 0173229 | 3/1986 |
| EP | 0336400 | 10/1989 |
| EP | 0669802 | 9/1995 |
| EP | 1228689 | 7/2002 |
| EP | 1479757 | 11/2004 |
| FR | 2858978 | 2/2005 |
| JP | 59067047 | 4/1984 |
| JP | 59101393 | 6/1984 |
| JP | 60193692 | 10/1985 |
| JP | 61263794 | 11/1986 |
| JP | 5162454 | 6/1993 |
| JP | 2002/256300 | 11/2002 |
| JP | 2004/339496 | 12/2004 |
| WO | WO 92/15662 | 9/1992 |
| WO | WO 93/17558 | 9/1993 |
| WO | WO 94/10842 | 5/1994 |
| WO | WO 96/15308 | 5/1996 |
| WO | WO 97/28791 | 8/1997 |
| WO | WO 97/34982 | 9/1997 |
| WO | WO 98/04555 | 2/1998 |
| WO | WO 00/06681 | 2/2000 |
| WO | WO 00/24958 | 5/2000 |
| WO | WO 00/45867 | 8/2000 |
| WO | WO 03/070666 | 8/2003 |
| WO | WO03/072151 | * 9/2003 |
| WO | WO 03/079786 | 10/2003 |
| WO | WO 03/086321 | 10/2003 |
| WO | WO 2004/078471 | 9/2004 |
| WO | WO 2004/098553 | 11/2004 |
| WO | WO 2005/030918 | 4/2005 |
| WO | WO 2005/031918 | 4/2005 |
| WO | WO 2005/034626 | 4/2005 |
| WO | WO 2005/046632 | 5/2005 |
| WO | WO 2005/048989 | 6/2005 |
| WO | WO 2005/099660 | 10/2005 |
| WO | WO 2005/108541 | 11/2005 |
| WO | WO 2006/011159 | 2/2006 |

* cited by examiner

DEODORIZING COMPOSITIONS

CROSS REFERENCE TO RELATED APPLICATIONS

Not applicable

REFERENCE REGARDING FEDERALLY SPONSORED RESEARCH OR DEVELOPMENT

Not applicable

SEQUENTIAL LISTING

Not applicable

BACKGROUND OF THE INVENTION

1. Field of the Invention

The present invention relates generally to deodorizers, and more particularly to deodorizers for textiles such as carpets, upholsteries, fabrics, and the like.

2. Description of the Background of the Invention

Compositions for treating fabric to remove stains, soils, and spilled liquids are known. One such composition is a granular composition that contains zeolite and a surfactant. The composition contains by percent weight of the composition 5.5% sodium sulfate, about 1% to about 20% of a perfume delivery composition, and a filler such as calcium carbonate. The perfume delivery composition in turn contains in weight percent of the perfume delivery composition about 10% to about 90% a natural or synthetic crystalline zeolite and about 5% to about 30% a perfume. The perfume also contains benzyl benzoate. The detergent composition can also have about 5% to about 80% an inorganic detersive builder such as sodium aluminosilicate.

A powdered cleaning composition for treating textiles contains by percent weight of the composition about 15% to about 90% zeolite and a brightener such as precipitated calcium carbonate. Yet another cleaning composition contains zeolite and an imide for removing stains and odors from a textile. The compositions have less than or equal to about 25% by percent weight of the composition a pH adjusting agent, a fragrance, a deodorizing agent, a filler, and a carrier that includes an inorganic salt. Another detergent composition is a bleach-stable deodorant composition containing perfume and zeolite. The zeolite acts as a detergency builder and is present from about 5% to about 75% by percent weight of the composition. Benzyl benzoate is a component of the perfume and present in an amount of 14.7 parts of the perfume.

A granular laundry composition having a release barrier contains by percent weight of the composition a perfume agent such as benzyl benzoate, a porous carrier such as a crystalline sodium aluminosilicate, 3.0% to 39.0% sodium sulfate, 5.0% calcium carbonate, and from about 0% to about 80% fillers, alkalinity sources, processing aids, and additional perfume ingredients. One such granular laundry composition contains from about 10% to about 80% a detergent builder such as sodium aluminosilicate.

In yet another detergent composition, a cellulase containing detergent composition contains sodium sulfate, a detergent builder such as sodium aluminosilicate and specifically zeolite, and a carbonate builder such as calcium carbonate.

Compositions containing zeolite and a surfactant for treating fabric with a first and second composition where heat is generated when the two compositions are combined to remove stains, soils, and spilled liquids are also known. The first composition includes anhydrous zeolite. Additive material such as an anhydrous inorganic salt is in the composition in an amount up to about 95% by percent weight of the composition.

A composition for cleaning carpet contains water, an ethoxylated glycerol type compound, a surfactant, an acaricidal compound, and a water insoluble hydrocarbon, essential oil, and a perfume. The acaricidal compound may be benzyl benzoate. An aqueous miticide composition contains about 0.01% to about 5% benzyl benzoate by percent weight of the composition, water, a solvent, and a surfactant. The amount of the organic solvent, surfactant and water are selected to maintain a stable dispersion of benzyl benzoate and organic solvent in an aqueous mixture.

A powdered fabric cleaner contains a carrier, silica, benzyl benzoate, and a fragrance. A carrier that can be used in the composition is sodium sulfate. An aqueous suspension medium for treating fabric includes a plurality of particles suspended therein. Each particle has a core consisting of a solid or liquid particle and a coating layer formed on the peripheral surface of the particle. The particles have a particulate mineral material or chemical such as zeolite and calcium carbonate. The aqueous suspension also includes benzyl benzoate, calcium carbonate, and an inorganic salt such as sodium sulfate.

Compositions containing benzyl benzoate as an active substance have also been used in insect control devices that hold an insect-repellent composition. Zeolite and calcium carbonate are present as inert absorbers or absorbers to retain the composition and release the composition gradually into the environment.

Therefore, there remains a need for additional deodorizing compositions that are applied to textiles that reduce or neutralize undesirable odors. A faster onset of action, a consistent particle size, a reduced application rate and/or a reduced frequency of application are also desired for deodorizing compositions that are applied to the textile. The discussion that follows discloses deodorizing compositions that help to fulfill these needs.

SUMMARY OF THE INVENTION

According to one aspect of the invention, a solid deodorizing composition is provided. The composition in one embodiment includes less than or equal to about 5% by weight a malodor counteractant comprising an ester compound, greater than or equal to about 95% by weight of at least one of an alkali metal inorganic salt and an alkaline-earth metal inorganic salt; and about 0.5% to about 50% by weight aluminosilicate.

According to yet another aspect of the invention, a method of deodorizing a textile is provided. Illustratively, the methods include providing a solid composition comprising about 0.01% to about 5% by weight an odor-counteracting material, greater than or equal to about 95% by weight of at least one of an alkali metal inorganic salt and an alkaline-earth metal inorganic salt, about 0.5% to about 50% by weight aluminosilicate, and a fragrance, and applying the solid composition to the textile.

In still another aspect of the invention, a solid deodorizing composition is provided that includes, for example, a malodor counteractant that comprises an ester compound and an inorganic salt in a weight to weight ratio of about 0.005:1 to about 0.05:1, and about 0.1% to less than about 2.5% by weight of the composition aluminosilicate.

Other aspects of the present invention will become apparent upon consideration of the following detailed description.

BRIEF DESCRIPTION OF THE DRAWINGS

Not applicable.

DETAILED DESCRIPTION

The present invention is directed to methods, kits, combinations, and compositions for reducing and/or eliminating a malodor from a textile. Malodors include such things as volatile, non-volatile, and semi-volatile organic molecules, odors caused by pets and bodily fluids such as sweat, urine, and vomit, smoke including cigarette smoke and cigar smoke, dampness, and mildew. The textiles include materials made of natural fibers, such as cotton and wool, regenerated natural fibers including regenerated cellulose, and materials made of synthetic organic fibers, such as acetate, polyacrylics, polyamides, polyester fibers, polyolefins, polyvinylidene chlorides, and/or rayon, and combinations thereof. Illustrative examples of textiles include carpets, upholstery, drapes, and fabrics such as clothing and furniture coverings. While the present invention may be embodied in many different forms, several specific embodiments are discussed herein with the understanding that the present disclosure is to be considered only as an exemplification of the principles of the invention, and it is not intended to limit the invention to the embodiments illustrated. Where the invention is illustrated herein with particular reference to a textile, it will be understood that any other similar material containing a malodorous molecule in need of treatment can, if desired, be substituted in whole or in part for the textile in the methods, kits, combinations, and compositions herein described.

The compositions of the present invention contain an effective amount of one or more odor-counteracting materials. Examples of odor-counteracting materials include an odor-absorbing agent, an odor-eliminating agent, a malodor-counteracting agent, and an odor-masking agent. An effective amount of an odor-counteracting material includes an amount sufficient to reduce and/or eliminate the concentration of an undesirable odor from a textile such that the level of the undesirable odor is reduced and/or eliminated in the surrounding environment. The odor-counteracting materials may also interact with the malodor in such a way that neutralizes the malodor, including chemically reacting with and/or absorbing a malodorous molecule. Illustratively, an odor-counteracting material may chemically react with a malodorous molecule in a way such as a polymerization reaction, an oxidization reaction, and/or a non-oxidization reaction. For example, one such chemical reaction converts a malodorous molecule such as a low molecular weight odoriferous fatty acid to an odorless salt. An odor-counteracting material may also mask the malodor. Typically, an odor-masking agent includes materials such as a perfume or a fragrance, which once in the air interacts with an olfactory system of a user such that a sense of the malodor is lost. An absorption process generally includes encapsulating or entrapping a malodorous molecule in a cavity or on a surface of a malodorous absorbing molecule. By reducing the concentration of the malodorous molecules associated with the textile through a chemical reaction, an absorption process, and/or a masking process, undesirable odors released into the air from the textile can be reduced and/or eliminated. A reduction or elimination of the odor from the air or surrounding environment can be measured by any technique known to those skilled in the art such as by using the human olfactory system to detect the odor present in the air.

In one embodiment of the present invention, a composition also includes one or more additives. Additives include, for example, a filling agent, a buffering agent, an optical brightener, a bleaching agent, a free flowing agent, an enzyme, an anticaking agent, a dye or colorant, an imide, an ultraviolet-absorbing agent, a preservative, an antibacterial agent, a germicidal agent, a preservative, a thickening agent, a chelating agent, a conditioning agent, a processing aid, a scattering promoter, an anti-soiling agent, a desiccant, a wetting agent, a humectant, a corrosion inhibitor, and/or an antistatic agent, and mixtures, combinations, and salts thereof. Other additives useful in the present invention include those described in, for example, *The Merck Index*, Merck & Co. Rahway, N.J., $13^{th}$ edition, 2001. Yet other additives useful in the present invention include those described in, for example, *McCutcheon's Detergents and Emulsifiers, North American Edition*, MC Publishing Co., 2005. Other additives useful in the present invention include those described in, for example, Kirk-Othmer, *Encyclopedia of Chemical Technology*, 5th Ed., Vol. 22, John Wiley & Sons, 2004. The additive may be present in an amount of about 0.1% to about 20% or more of the total weight of the composition.

Illustratively, a composition of the present invention includes an effective amount of a salt, at least one odor-counteracting material including a malodor counteractant, an odor absorbent, and an odor-masking agent, and an optional additive.

The salt in one embodiment of the present invention is an inorganic salt. Inorganic salts useful in the present invention include alkali metal and alkaline-earth metal salts of sulfates, chlorides, carbonates, bicarbonates, citrates, phosphates, and/or nitrates including, for example, sodium bicarbonate, sodium borate, sodium carbonate, sodium chloride, sodium citrate, sodium nitrate, sodium sulfate, sodium tripolyphosphate, and calcium carbonate, and mixtures and combinations thereof. An effective amount of a salt includes from about 1% to about 99%, or about 50% to about 98%, or about 90% to about 97%, or greater than or equal to about 90%, or greater than or equal to about 95%, or greater than or equal to about 97%, by weight percent of the composition. Depending on the application of the salt, the salt may act as, for example, a filler and/or an odor absorbent. Mixtures and combinations of the above mentioned inorganic salts can also be used in the methods, kits, combinations, and compositions herein described.

In one embodiment, the malodor counteractant is a compound that is capable of reacting with and/or neutralizing a malodor. One such compound useful in the present invention includes, for example, an ester compound such as a compound containing the grouping, —X(O)—O—R, where X is carbon, sulfur, or phosphorus, and R is a radical of an alcohol. When present in the composition, the malodor counteractant is typically present in an amount effective to neutralize one or more malodors associated with the textile such that the concentration of the malodor in the surrounding air is reduced and/or eliminated. Typical effective amounts of a malodor counteractant include from about 0.01% to about 99%, or about 0.05% to about 50%, or about 0.1% to about 10%, or about 0.25% to about 5%, or about 0.5% to about 2.5%, or less than or equal to about 5%, or less than or equal to about 2.5%, or less than or equal to about 1%, or less than or equal to about 0.75%, or less than or equal to about 0.5%, by weight percent of the composition. In other embodiments, the amount of the malodor counteractant is present in a deodorizing composition of the present invention in an amount that when applied to the textile, the malodor counteractant neutralizes an amount of the malodor associated with the textile such that an undesirable odor emanating from the textile is reduced compared to a composition without the malodor counteractant. Illustratively, a malodor counteract of the present invention includes amyl cinnamaldehyde, benzophenone, benzyl benzoate, benzyl isoeugenol, benzyl phenyl acetate, benzyl salicylate, butyl cinnamate, cinnamyl butyrate, cinnamyl isovalerate, cinnamyl propionate, decyl acetate, ethyl myristate, isobutyl cinnamate, isoamyl salicylate, phenethyl benzoate, phenethyl phenyl acetate, triethyl citrate, and tripropylene glycol n-butyl ether. Without wishing to be bound by theory, when benzyl benzoate or a similar liquid malodor counteractant is present in a composition of the present invention, it is believed that upon application of the composition to the textile, the surface of the textile is coated with a thin liquid film of the benzyl benzoate, which acts as a high surface area absorption and/or reaction site for malodors associated with the textile. Mixtures and combinations of the above mentioned malodor counteractants can be used in the methods, kits, combinations, and compositions herein described.

Illustratively, the odor absorbent useful in the present invention is an aluminosilicate or a salt thereof. For example, the aluminosilicate is a natural or synthetic zeolite mineral having a formula of, for example, $M_{2/n}O\, Al_2O_3\, ySiO_2\, wH_2O$, where M is a group IA or IIA metal, n is the cation valence, y is 2 or greater and w is the number of channels or interconnected voids within the zeolite. See, *The Merck Index*, $12^{th}$ Edition, 10250, (1996). Examples of a group IA metal include lithium, sodium, and potassium. Examples of a group IIA metal include magnesium and calcium. A commercially available zeolite is Zeolex® 23A, supplied by J. M. Huber Company. Other useful zeolites include "13X", available as Type 13X from Linde or Davison, having structure type X and a pore size of 10 Angstroms; zeolite "4A", available as Type 4A from Linde or Davison, having structure Type A and a pore size of 4 Angstroms; Sipernat 820A from Degussa; Alusil ET from Lineos; and zeolite NaX and zeolite NaA, available as Linde ZB100 and Linde ZLB1000, respectively, both supplied by Union Carbide. Other aluminosilicates useful in the present invention include those described in, for example, U.S. Pat. No. 4,493,781, assigned to S.C. Johnson & Son, Inc. Yet other aluminosilicates useful in the present invention include those described in, for example, U.S. Pat. No. 2,882,243. Modified zeolite-type materials can also be used in the present invention, such as the manganese-aluminum-phosphorus-silicon-oxide molecular sieves and other zeolite odor-absorbing compositions as described in, for example, U.S. Pat. No. 4,793,833. Other zeolite-type materials useful in the present invention include those described in, for example, U.S. Pat. No. 4,604,110. Yet other zeolite-type materials useful in the present invention include those described in, for example, U.S. Pat. No. 4,437,429. Still other zeolite-type materials useful in the present invention include those described in, for example, U.S. Pat. No. 4,648,977. Other zeolite-type materials useful in the present invention include those described in, for example, U.S. Pat. No. 4,648,882. Yet other zeolite-type materials useful in the present invention include those described in, for example, U.S. Pat. No. 4,493,781. Still other zeolite-type materials useful in the present invention include those described in, for example, U.S. Pat. No. 5,286,400. Yet other zeolite-type materials useful in the present invention include those described in, for example, U.S. Pat. No. 4,795,482. Other zeolite-type materials useful in the present invention include those described in, for example, U.S. Pat. No. 4,826,497. Yet other zeolites useful in the present invention include those described in, for example, U.S. Pat. No. 6,284,232. Still other zeolites useful in the present invention include those described in, for example, U.S. Patent Application Publication No. 2005/0037937. The aluminosilicate may be supplemented with dry hydrated colloidal silica if desired. Depending on the application of the aluminosilicate, the aluminosilicate may act as a free flowing agent and/or an anticaking agent as well as an odor absorbent. Typical effective amounts of the odor absorbent include from about 0.001% to about 99%, or about 0.05% to about 50%, or about 0.1% to about 20%, or about 0.5% to about 10%, or less than or equal to about 10%, or less than or equal to about 2.5%, or less than or equal to about 1.5%, or less than or equal to about 0.75%, by percent weight of the composition. For example, a composition of the present invention has an effective amount of the odor absorbent from about 0.001% to less than about 5% or from about 0.01% to less than about 2.5% by percent weight of composition. Illustratively, the average particle size of the aluminosilicate based on weight ranges from about 1 millimicron to about 100 microns, or from about 3 microns to about 80 microns, or from about 5 microns to about 40 microns. Other odor absorbents useful in the present invention include a clay, diamataceous earth, bentonite, sand, silica, and/or polymeric materials. Mixtures and combinations of the above mentioned odor absorbents can be used in the methods, kits, combinations, and compositions herein described.

In one embodiment of the present invention the odor-masking agent is a perfume or fragrance. A fragrance may be naturally or synthetically produced and may be added to the composition in any conventional manner known to those skilled in the art including, for example, admixing to the composition or blending with other constituents used to form the composition. When present in the composition, an odor-masking agent is present, for example, in an effective amount useful to enhance and/or impart a desired scent characteristic to the composition and/or to interact with the olfactory system of the user such that the sense of the malodor by the user is reduced or eliminated. Typical effective amounts of the fragrance in a composition of the present invention include from about 0.01% to about 20%, or about 0.1% to about 10%, or about 0.25% to about 5%, or about 0.5% to about 2.5%, or about 0.75% to about 1.5%, or less than or equal to about 5%, or less than or equal to about 2.5%, or less than or equal to about 1%, or less than or equal to about 0.75%, or less than or equal to about 0.5%, by percent weight of the composition. A useful fragrance in the present invention is in an aromatic liquid or solid that vaporizes and dispenses in air. Illustrative examples of fragrances and perfumes include compositions available from Takasago International Corporation, including, for example, Country Garden (330631 Takasago RM-3054), Melon Burst (330688 Takasago RN-376), Tropical Mist (330795 Takasago RP-1503), and 330178 Takasago RB 1907/A for pet odors, and from Quest International, including, for example, Lilac Spring (330859 Quest Q35105), Rainshower (330860 Quest Q35143), Neutralizer (330319 Quest Q-13231), French Vanilla (330813 Quest Q-33280), Linen (330832 Quest Q34966), and Suddenly Spring (Quest Q37472). Other fragrances useful in the present invention include those described in, for example, U.S. Patent Application No. 2005/0145711. Mixtures and combinations of the above-mentioned odor-masking agents can be used in the methods, kits, combinations, and compositions herein described.

Illustratively, a composition of the present invention comprises greater than or equal to about 95% an inorganic salt, about 0.5% to about 10% a malodor counteractant, about 1% to about 20% an odor absorbent, and an odor-masking agent in an amount of about 0.5% to about 10%, by percent weight of the composition. In yet another embodiment, a composition comprises greater than or equal to about 97% an inorganic salt, about 0.75% to about 5% a malodor counteractant, about 1.5% to about 10% an odor absorbent, and an optional fragrance in an amount of about 0.75% to about 5%, by percent weight of the composition. In yet another embodiment of the present invention, the composition comprises greater than or equal to about 97% an inorganic salt, less than or equal to about 0.75% a malodor counteractant, less than or equal to about 1.5% an odor absorbent, and an optional fragrance in an amount less than or equal to about 0.75%, by percent weight of the composition. A composition of the present invention may also contain an amount of an inorganic salt, a malodor counteractant, and odor absorbent, and an odor-masking agent sufficient to reduce and/or an eliminate odor associated with the textile. Illustratively, the weight to weight ratio of the malodor counteractant to the odor absorbent in a composition of the present invention ranges from about 0.025:1 to about 1:1, or about 0.05:1 to about 0.75:1, or is about 0.25:1, or about 0.5:1, or about 0.75:1. In another embodiment, the weight to weight ratio of the malodor counteractant to the inorganic salt ranges from about 0.0025:1 to about 0.1:1, or about 0.005:1 to about 0.05:1, or is about 0.006:1, or about 0.007:1 to about 0.008:1.

The composition in one embodiment of the present invention is a solid. A solid composition includes, for example, a powder of ground, pulverized, or otherwise finely dispersed solid particles. Further, in one embodiment, the solid composition of the present invention is readily dispersible, such as a flowable granular composition that can be dispersed onto a surface from a device suitable for applying the composition to the surface. Such devices include such things as a container with holes or perforations that are sized to allow passage of the composition when the container is shaken and/or poured by the user. Illustrative containers useful to hold and/or disperse a composition of the present invention include those disclosed in Ser. No. 11/249,676, filed on Oct. 13, 2005, the disclosure of which is herein incorporated by reference. Other illustrative containers useful to hold and/or disperse a composition of the present invention include those disclosed in Ser. No. 11/249,843, filed on Oct. 13, 2005, the disclosure of which is herein incorporated by reference.

A composition of the present invention may also contain water or be substantially void of water. Illustratively, a composition includes an amount of water that does not promote agglomeration of the composition when dispersed onto the textile, but allows the composition to be applied to the textile in a substantially uniform manner. For example, if a solid composition is desired and the composition is too dry, the composition may be too powdery and may tend to be blown by wind currents, thus potentially limiting deposition of the composition onto the textile surface. However, if the composition is too wet, the composition can agglomerate and when dispersed from a container be deposited on the textile in a non-uniform manner. Illustratively, a composition of the present invention may be moist to the touch and not feel particularly powdery or dusty. Such a composition when dispersed from the container when shaken disperses substantially uniformly into small particles onto the surface of the textile. When the appropriate amount of water is present, these small particles generally remain on the surface of the textile without a tendency to be blown from the surface by breezes or other air currents experienced in a home, for example. Water may be present in very small amounts, including amounts suitable for water of hydration of one or more materials of the composition, or in larger amounts such as from about 0.1% to about 5% or more of the weight of the composition. Water of hydration includes water that is chemically combined with a material in such a way that it can be removed, as by heating, without substantially changing the chemical material of the substance. Also, if too much water is present in the composition when applied to the textile, a drying period may be required before excess composition can be removed from the textile through, for example, vacuuming or brushing. Moisture content of the composition may be determined by those skilled in the art using such methods titrimetry, for example, Karl Fisher titration, and/or gravimetry, for example, thermal gravimetric analysis.

The compositions of the present invention typically exhibit a bulk density from about 0.9 grams to about 1.8 grams per cubic centimeter of volume, a loose density from about 1.3 to about 1.5 grams per cubic centimeter of volume, and/or a packed density of between about 1.6 grams to about 1.8 grams per cubic centimeter of volume. Illustratively, the bulk density of a composition of the present invention is not so low as to render the composition too powdery and therefore difficult to dispense in desired amounts from a dispensing device and/or to make it too dusty when applied to the textile. Also, the bulk density in one embodiment is not too high so as to make the composition too heavy and/or difficult to uniformly disperse from the dispensing device.

If necessary to adjust the pH of a composition of the present invention to a desired pH, acidic and alkaline buffering agents known to those skilled in the art can be used.

An antimicrobial agent useful in the present invention includes, for example, sodium benzoate, sodium propionate, dialkyl ($C_8$-$C_{18}$) dimethyl ammonium chloride, and salts of undecylenic acid.

Useful antisoiling agents include, for example, aliphatic quaternary ammonium salts, aluminum oxides, cationic amines, colloidal silica, imidazoline salts, fluorochemicals, polyvinylpyrrolidone, polyacrylates, styrene-maleic anhydride copolymer resins, and vinyl acetate/maleic anhydride.

Hydrogen peroxide is a useful bleaching agent that may be used in a composition of the present invention. Other bleaching agents useful in the present invention include those described in, for example, U.S. Pat. No. 4,663,068.

A brightening agent useful in the present invention includes alumina, alumina hydrate, clays such as bentonite, kaolin and the like, distyrylbiphenyl derivatives, magnesium silicate, precipitated calcium carbonate, talc, and stilbene derivatives.

A chelating agent useful in the present invention includes, for example, an aminopolycarboxylic acid, such as ethylenediaminetetraacetic acid, diethylenetriaminepentaacetic acid, and N-hydroxyethylethylenediaminetriacetic acid.

A desiccant useful in the present invention includes a substance with a high affinity for water such as calcium oxide or silica gel, which may be used as a drying agent.

Suitable enzymes useful in the present invention include those described in, for example, U.S. Pat. No. 6,881,712. Other suitable enzymes useful in the present invention include those described in, for example, U.S. Statutory Invention Registration No. H1468.

A filler useful in the present invention includes talc and naturally occurring or synthetic clays, for example, smectite clays, montmorillonites, sodium saponites, and sodium hectorites.

An imide useful in the present invention includes those described in, for example, U.S. Pat. No. 6,284,232.

Preservatives useful in the present invention include a paraben such as methyl paraben and ethyl paraben.

A composition of the present invention can be made by any method known to those skilled in the art, including, for example, a granulating process such as agglomeration, spray-drying, extrusion, fluid-bed agglomeration, roll-compaction, freeze-drying, tabletting, a mix Muller process, a pin mixer process, and/or a batch tumble blending mixer process. Agglomeration is the process of bringing together fine powders or particulates into larger masses with pressure, agitation, and/or other mechanisms. Agglomerating techniques include: (1) pressure compacting, such as briquetting, tabletting, and using a pellet mill; (2) tumbling or granulation; and (3) spray congealing. Agglomeration processes useful in the present invention includes the methods described in, for example, U.S. Pat. No. 6,576,601, assigned to S.C. Johnson & Son, Inc.

Illustratively, a powdered composition of the present invention may be made by introducing at least one particulate material into a mixing vessel, introducing at least one liquid material into the mixing vessel to form a mixture, blending the mixture for a first time period, chopping the mixture for at least a portion of the first time period, and thereafter blending the mixture without chopping for a second time period. The method produces a particulate composition having acceptable flow characteristics and level of fines In one illustrative process of the present invention, sodium sulfate is charged to a mixer. Perfume and benzyl benzoate are premixed for 5 sec to 10 min. The mixer is started and the premixture of perfume and benzyl benzoate is added to the mixer containing the sodium sulfate. Zeolex® is then charged to the mixer and the mixture is blended for a period of time lasting less than about one minute to greater than about one quarter of an hour until uniform.

In another illustrative process, sodium sulfate is charged to a mixer. The mixer is then started and a perfume is charged to the mixer and blended. Benzyl benzoate is then charged to the mixer and blended with the sodium sulfate and perfume mixture. Zeolex is then charged to the mixer and the mixture is blended for a period of time lasting less than about one minute to greater than about one quarter of an hour until uniform.

In an alternative process, sodium sulfate and Zeolex® are charged to a mixer. The mixer is started, and a perfume is charged to the sodium sulfate and Zeolex® mixture and blended. Benzyl benzoate is then charged to the mixer and the mixture is blended for a period of time lasting less than about one minute to greater than about one quarter of an hour until uniform.

In yet another illustrative process, sodium sulfate and Zeolex® are charged to the mixer and blended. Perfume and benzyl benzoate are premixed for 5 sec to 10 min. and then charged to the mixture of the sodium sulfate and Zeolex®. The mixture is blended for a period of time lasting less than about one minute to greater than about one quarter of an hour until uniform.

Other methods of preparation of the powdered formulation of the present invention may also be employed known to those skilled in the art.

A solid composition of the present invention can be formulated to have a desired particle size dependent upon the nature of the textile surface and the desired use thereof such as the desire to remove any excess composition from the textile by vacuuming. For example, when applying a composition to a carpet the average particle size based on weight may be less than or equal to about 1500 microns, less than or equal to about 1200 microns, less than or equal to about 1000 microns, less than or equal to about 800 microns, or less than or equal to about 400 microns, and/or greater than or equal to about 5 microns, greater than or equal to about 15 microns, greater than or equal to about 30 microns, or greater than or equal to about 45 microns. Illustratively, the average particle size based on weight of the composition ranges from about 5 microns to about 1500 microns, or from about 15 microns to about 1200 microns, or from about 30 microns to about 800 microns. Without wishing to be bound by theory, it is believed that smaller sized particles are easier to remove from a textile by vacuuming or other mechanical processes. Therefore, where a composition is applied to a textile or other surface in which excess composition is to be mechanically removed, a smaller sized particle size may be desirable in such applications. Average particle size by weight may be determined by measuring the average particle weight and calculating the particle diameter of this weight.

A solid deodorizing composition of the present invention may be prepared using the following ingredients:

| Ingredient | Weight kg. (lbs.) | Weight percent |
|---|---|---|
| Sodium sulfate | 44 kg (97 lbs.) | 97 |
| Sodium aluminosilicate | 0.68 kg (1.5 lbs.) | 1.5 |
| Benzyl benzoate | 0.34 kg (0.75 lbs.) | 0.75 |
| Fragrance (Quest Q-35143, manufactured by Quest International) | 0.34 kg (0.75 lbs.) | 0.75 |
| Total | 45.36 kg (100 lbs.) | 100 |

A method of using a deodorizing composition to remove at least one malodor from a textile is also provided by the present invention. For example, a composition containing an inorganic salt, at least one of a malodor counteractant, an odor absorbent, and an odor-masking agent, and an optional additive is provided in a solid composition to remove a malodor from the textile. The composition is applied to the textile, and excess may be removed after a desired period of time.

In an additional embodiment of the present invention, a process for removing a malodor from a textile is provided. The method includes applying an amount of a composition of the present invention to the textile at or near the location of the malodor and removing excess amounts of the composition from the textile. The excess composition may be removed from the textile by, for example, vacuuming or brushing, after a period of time has elapsed.

A typical method of applying a composition of the present invention to the textile includes dispersing or scattering the composition by hand or by a suitable device such as a shaker-type container onto the textile at or near the location of the malodor. Other ways of dispensing a composition of the present invention including for example, a dry powder or a slurry composition, are known to those skilled in the art and include from a pressurized aerosol container or from a trigger or pump activated sprayer. A composition of the present invention in one embodiment is readily dispersed from a dispensing container as small, non-powdery particles. Such particles when applied to the textile tend to remain on the surface of the textile and generally do not substantially drift from the surface when exposed to air currents found in a home environment, for example. If desired, the compositions may be physically or mechanically rubbed or interspersed on the textile to facilitate contact with the textile and/or the malodor. The composition in one embodiment is applied to the textile at a rate from about 2.5 g/foot$^2$ to about 50 g/foot$^2$, or about 5 g/foot$^2$ to about 25 g/foot$^2$, or about 10 g/foot$^2$ to about 20 g/foot$^2$, or about 10 g/foot$^2$, or about 15 g/foot$^2$, or about 17.5 g/foot$^2$, or about 20 g/foot$^2$, or about 25 g/foot$^2$. The application rate depends on factors such as the particular textile being treated, the surface area of the treated textile in a given area, and/or the type of malodor treated. The composition is allowed to rest or settle on the textile for a desired period of time to allow the malodors to be neutralized, masked, and/or absorbed by the odor-counteracting material or materials contained in the composition. In one embodiment, after the desired period of time such as, for example, less than about 30 seconds, less than about 1 minute, less than about 2 minutes, less than about 5 minutes, less than about 10 minutes, less than about 15 minutes, less than about 30 minutes, less than about 45 minutes, less than about 1 hour, less than about 2 hours, less than about 8 hours, less than about 12 hours, or less than about 24 hours, or longer, any residue or excess composition is removed from the textile by, for example, a mechanical process such as vacuuming and/or brushing.

Other than being used as a composition that is sprinkled onto the textile, it is also contemplated that the compositions of the present invention may be utilized to neutralize, mask, and/or absorb malodors in, for example, solid or liquid carpet cleaners, floor cleaners, bathroom cleaners, laundry detergents, and/or cat litter. The compositions of the present invention can also be packaged in an appropriate package for use as, for example, a car freshener, a refrigerator deodorizer, and/or a freezer deodorizer, or to deodorize an area or space such as musty closets, coolers, diaper pails, and/or garbage cans.

In another embodiment of the present invention, a kit is provided containing one or more compositions of the present invention. The kits may contain for example a dispenser such as a container, the composition, and/or a set of instructions for a user. The composition or compositions can be packaged in the form of a container such as a canister, jar, bottle, and the like, which contains a single application or a plurality of applications for a given area.

The present invention is further illustrated by the following example, which should not be construed as limiting in any way. The experimental procedures to generate the data shown are discussed in more detail below. The terms "parts by weight" or "weight percent" are used interchangeably in the specification and in the following example.

EXAMPLE 1

Malodor Elimination Study

Compositions of the present invention were tested for the ability to eliminate four common household odors including a cat urine malodor, a wet dog malodor, a musty mildew malodor, and a cigarette malodor from carpet swatches. The compositions tested include Formulas A-D shown below in Table No. 1. Formula A was provided as a control formula.

TABLE NO. 1

Weight percent of Tested Formulas

| Chemical Name | Weight Percent | | | |
| --- | --- | --- | --- | --- |
| | A | B | C | D |
| Sodium sulfate | 97.75 | 97.45 | 98 | 97 |
| Sodium aluminosilicate | 1.5 | 1.5 | 1.5 | 1.5 |
| Benzyl benzoate | — | — | — | 0.75 |
| Fragrance ("light fresh floral") | 0.75 | 1.05 | 0.5 | 0.75 |

About 90 consumer testers were recruited and exposed to each formula and malodor combination. Screening criteria for the consumer testers included female heads of household ages 18 to 55, ethnicity of at least fifteen self-identified Hispanics, experience with all four of the malodors within the past year, no aversion to smelling the malodors, and no aversion to smelling a "light fresh floral" scented carpet powder. A given tester was allowed, but not required, to participate in all four malodor tests. The tests took place over 4 days. On each day each tester of the panel was exposed to all four formulas in conjunction with one of the four malodors. There were 2 test sessions each day:

Test day 1: wet dog
Test day 2: cigarette smoke
Test day 3: cat urine
Test day 4: musty mildew Each test session lasted 60 minutes.

Each tester was exposed to 4 test stations. At each test station there were 3 jars:

Jar 1: Reference—The malodor only as the "reference"
Jar 2: Treated—The malodor treated with a test formula
Jar 3: Untreated—The malodor only Testers took a 1 minute break in-between visits to each of the test stations.

Testers were instructed to sniff the reference Jar 1 first and were told that this is the odor they are being asked to detect in the other jars. Testers were then asked if they detected any malodor in the reference jar and if so, how strong it was. Data collected from testers who reported they could not detect any malodor in the reference Jar 1 were not included in the final analysis.

At each station, after the testers sniffed the reference Jar 1, testers sniffed the other two jars in a randomized order. For these jars, testers were asked if they detected any malodor (Yes/No) and, if they did, to rate the strength of the odor on a 9-point scale (1=very weak, 9=very strong). The results are shown below in Tables Nos. 2-5.

TABLE NO. 2

Detection and Rating Results for Cat Urine Malodor, Sample size = 86

| Questionnaire Item | Malodor | Formula | | | |
| --- | --- | --- | --- | --- | --- |
| | | A | B | C | D |
| Do you smell a cat odor in this jar? (% Yes) | Reference | 97 | 100 | 99 | 98 |
| | Untreated | 91 | 98 | 95 | 95 |
| | Treated | 30 | 17 | 28 | 13 |
| If you answered "yes", how would you rate the strength of the cat odor in this jar? | Reference | 5.9 | 5.7 | 5.8 | 5.0 |
| | Untreated | 5.2 | 5.1 | 5.6 | 4.9 |
| | Treated | 2.4 | 2.5 | 2.6 | 3.8 |

TABLE NO. 3

Detection and Rating Results for Wet Dog Malodor, Sample size = 87

| Questionnaire Item | Malodor | Formula | | | |
| --- | --- | --- | --- | --- | --- |
| | | A | B | C | D |
| Do you smell a dog odor in this jar? (% Yes) | Reference | 98 | 99 | 98 | 98 |
| | Untreated | 97 | 98 | 97 | 98 |
| | Treated | 38 | 15 | 39 | 18 |

TABLE NO. 3-continued

Detection and Rating Results for Wet Dog Malodor, Sample size = 87

| Questionnaire Item | Malodor | Formula A | B | C | D |
|---|---|---|---|---|---|
| If you answered "yes", how would you rate the strength of the dog odor in this jar? | Reference | 6.0 | 6.3 | 6.6 | 6.5 |
| | Untreated | 5.4 | 6.1 | 5.3 | 5.8 |
| | Treated | 2.3 | 2.9 | 2.5 | 2.6 |

TABLE NO. 4

Detection and Rating Results for Musty Mildew Malodor, Sample size = 86

| Questionnaire Item | Malodor | Formula A | B | C | D |
|---|---|---|---|---|---|
| Do you smell a musty mildew odor in this jar? (% Yes) | Reference | 94 | 99 | 99 | 98 |
| | Untreated | 91 | 98 | 93 | 99 |
| | Treated | 22 | 15 | 20 | 17 |
| If you answered "yes", how would you rate the strength of the musty mildew odor in this jar? | Reference | 4.7 | 5.1 | 5.0 | 5.1 |
| | Untreated | 4.2 | 5.0 | 4.5 | 4.3 |
| | Treated | 3.1 | 2.9 | 2.9 | 2.3 |

TABLE NO. 5

Detection and Rating Results for Cigarette Smoke Malodor, Sample size = 91

| Questionnaire Item | Malodor | Formula A | B | C | D |
|---|---|---|---|---|---|
| Do you smell a smoke odor in this jar? (% Yes) | Reference | 99 | 98 | 99 | 99 |
| | Untreated | 95 | 91 | 96 | 95 |
| | Treated | 30 | 21 | 35 | 19 |
| If you answered "yes", how would you rate the strength of the smoke odor in this jar? | Reference | 5.8 | 5.9 | 6.0 | 5.8 |
| | Untreated | 4.6 | 4.4 | 5.4 | 4.9 |
| | Treated | 3.1 | 2.3 | 2.3 | 2.6 |

The carpet swatch used in the study was made of 100% nylon and cut into 5"×5" squares. The cat, dog, and musty mildew malodors were applied to the carpet swatches about 25 hours prior to test time. The cigarette malodor was applied to the carpet swatches a few hours before the first test session. The cigarette malodor carpet swatches were stored in aluminum foil until they were treated with the test formulas. About 1 hour prior to the start of the test session, the treated carpet squares were sprinkled with 3 grams of each test formula. A Test Administrator waited 15 minutes before vacuuming the squares. The squares were then placed into one-gallon glass jars and covered before testing.

INDUSTRIAL APPLICABILITY

The present invention in one embodiment provides a deodorizer composition useful for reducing or eliminating odors. For example, the deodorizer composition reduces or neutralizes a malodor associated with a textile for an appropriate length of time. The deodorizer compositions are easy for a user to apply and may be formulated such that any excess composition is removed by a mechanical process such as vacuuming or brushing.

The invention has been described in an illustrative manner, and it is to be understood that the terminology used is intended to be in the nature of description rather than of limitation. All patents, patent applications, and other references cited herein are incorporated herein by reference as if they appear in this document in their entirety. Many modifications, equivalents, and variations of the present invention are possible in light of the above teachings. Therefore, it is to be understood that within the scope of the appended claims, the invention may be practiced other than as specifically described.

I claim:

1. A solid deodorizing composition consisting of:
    about 0.5% to about 2.5% by weight a malodor counteractant selected from the group consisting of amyl cinnamaldehyde, benzophenone, benzyl benzoate, benzyl isoeugenol, benzyl phenyl acetate, benzyl salicylate, butyl cinnamate, cinnamyl butyrate, cinnamyl isovalerate, cinnamyl propionate, decyl acetate, ethyl myristate, isobutyl cinnamate, isoamyl salicylate, phenethyl benzoate, phenethyl phenyl acetate, triethyl citrate, tripropylene glycol n-butyl ether, and combinations thereof;
    greater than or equal to about 95% by weight of at least one of an alkali metal inorganic salt and an alkaline-earth metal inorganic salt;
    about 0.5% to about 5% by weight aluminosilicate; and
    an odor masking agent.

2. The composition of claim 1, wherein the inorganic salt is at least one of an alkali metal salt or an alkaline-earth metal salt of a sulfate and a carbonate.

3. The composition of claim 2, wherein the inorganic salt is in an amount greater than or equal to about 97% by weight of the composition.

4. The composition of claim 1, wherein the aluminosilicate is sodium aluminosilicate and present in the composition in an effective amount to counteract a malodor when the composition is applied to a textile.

5. The composition of claim 4, wherein the sodium aluminosilicate is a zeolite.

6. The composition of claim 5, wherein the zeolite is present in an amount less than or equal to about 2.5% by weight of the composition.

7. The composition of claim 1, wherein the malodor counteractant is benzyl benzoate and is present in the composition in an amount less than or equal to about 1% by weight of the composition.

8. The composition of claim 1, wherein the odor masking agent is present in the composition in an amount of about 0.5% to about 2.5% by weight of the composition.

9. A solid deodorizing composition, consisting of:
    a malodor counteractant selected from the group consisting of amyl cinnamaldehyde, benzophenone, benzyl benzoate, benzyl isoeugenol, benzyl phenyl acetate, benzyl salicylate, butyl cinnamate, cinnamyl butyrate, cinnamyl isovalerate, cinnamyl propionate, decyl acetate, ethyl myristate, isobutyl cinnamate, isoamyl salicylate, phenethyl benzoate, phenethyl phenyl acetate, triethyl citrate, tripropylene glycol n-butyl ether, and combinations thereof and an inorganic salt in a weight to weight ratio of about 0.005:1 to about 0.025:1;
about 0.1% to less than about 2.5% by weight of the composition aluminosilicate and
an odor masking agent.

10. The composition of claim 9, wherein the inorganic salt is present in an amount greater than or equal to about 95% by weight of the composition.

11. The composition of claim 10, wherein the inorganic salt is at least one of an alkali metal salt and an alkaline-earth metal salt of a sulfate and a carbonate.

12. The composition of claim 9, wherein the malodor counteractant is benzyl benzoate and present in the composition in an amount from about 0.5% to about 2.5% by weight of the composition.

13. The composition of claim 1, wherein the solid composition is formulated to have a bulk density from about 0.9 grams to about 1.8 grams per cubic centimeter of volume.

14. A solid deodorizing composition consisting of:
a liquid malodor counteractant in an amount effective to neutralize one or more malodors associated with a textile, wherein the concentration of the one or more malodors in air surrounding the textile is reduced;
greater than or equal to about 90% by weight an inorganic salt selected from the group consisting of sodium borate, an alkali metal salt of sulfates, chlorides, carbonates, bicarbonates, citrates, phosphates, and nitrates, an alkaline-earth metal salt of sulfates, chlorides, carbonates, bicarbonates, citrates, phosphates, and nitrates, and combinations thereof;
less than or equal to about 10% by weight aluminosilicate or a salt thereof; and
an odor masking agent.

15. The composition of claim 14, wherein the liquid malodor counteractant is an ester.

16. The composition of claim 14, wherein the liquid malodor counteractant is selected from the group consisting of amyl cinnamaldehyde, benzophenone, benzyl benzoate, benzyl isoeugenol, benzyl phenyl acetate, benzyl salicylate, butyl cinnamate, cinnamyl butyrate, cinnamyl isovalerate, cinnamyl propionate, decyl acetate, ethyl myristate, isobutyl cinnamate, isoamyl salicylate, phenethyl benzoate, phenethyl phenyl acetate, triethyl citrate, tripropylene glycol n-butyl ether, and combinations thereof.

17. The composition of claim 14, wherein the malodor associated with the textile comprises at least one of a cat urine malodor, a musty mildew malodor, a cigarette smoke malodor, or a wet dog malodor.

18. The composition of claim 14, wherein the liquid malodor counteractant is present in an amount of less than or equal about 2.5% by weight of the composition.

* * * * *